US012606807B2

(12) United States Patent
Yamaguchi et al.

(10) Patent No.: US 12,606,807 B2
(45) Date of Patent: Apr. 21, 2026

(54) METHOD FOR PURIFYING PROTEIN DERIVED FROM MEMBRANE PROTEIN COMPLEX

(71) Applicants: SUMITOMO RUBBER INDUSTRIES, LTD., Kobe (JP); TOHOKU UNIVERSITY, Sendai (JP)

(72) Inventors: Haruhiko Yamaguchi, Kobe (JP); Yukino Inoue, Kobe (JP); Seiji Takahashi, Sendai (JP); Toru Nakayama, Sendai (JP)

(73) Assignees: SUMITOMO RUBBER INDUSTRIES, LTD., Kobe (JP); TOHOKU UNIVERSITY, Sendai (JP)

( * ) Notice: Subject to any disclaimer, the term of this patent is extended or adjusted under 35 U.S.C. 154(b) by 337 days.

(21) Appl. No.: 18/283,332

(22) PCT Filed: Mar. 23, 2022

(86) PCT No.: PCT/JP2022/013633
§ 371 (c)(1),
(2) Date: Sep. 21, 2023

(87) PCT Pub. No.: WO2022/220042
PCT Pub. Date: Oct. 20, 2022

(65) Prior Publication Data
US 2024/0174989 A1     May 30, 2024

(30) Foreign Application Priority Data
Apr. 16, 2021    (JP) ................................. 2021-069637

(51) Int. Cl.
*C12N 9/10* (2006.01)
*C07K 1/36* (2006.01)

(52) U.S. Cl.
CPC .............. *C12N 9/1085* (2013.01); *C07K 1/36* (2013.01)

(58) Field of Classification Search
CPC .......... C07K 1/14; C12N 9/10; C12N 9/1085
See application file for complete search history.

(56) References Cited

U.S. PATENT DOCUMENTS

| | | | |
|---|---|---|---|
| 2009/0275066 A1 | 11/2009 | Popot et al. | |
| 2009/0324650 A1 | 12/2009 | Legon et al. | |
| 2010/0278880 A1 | 11/2010 | Legon et al. | |
| 2013/0023026 A1 | 1/2013 | Popot et al. | |
| 2016/0030553 A1 | 2/2016 | Legon | |
| 2018/0355000 A1* | 12/2018 | Yamaguchi | C12N 15/09 |
| 2021/0130385 A1 | 5/2021 | Falson et al. | |

FOREIGN PATENT DOCUMENTS

| | | | |
|---|---|---|---|
| JP | 2010-509602 A | 3/2010 | |
| JP | 2020-510026 A | 4/2020 | |
| WO | 2017/002504 A1 | 1/2017 | |

OTHER PUBLICATIONS

Juarez et al., "From polymer chemistry to structural biology: The development of SMA and related amphipathic polymers for membrane protein extraction and solubilisation," Elsevier, Chemistry and Physics of Lipids, vol. 221, 2019, pp. 167-175.
Asawatreratanakul et al., "Molecular cloning, expression and characterization of cDNA encoding cis-prenyltransferases from Hevea brasiliensis," European Journal of Biochemistry, vol. 270, 2003, pp. 4671-4680.

* cited by examiner

*Primary Examiner* — Tekchand Saidha
(74) *Attorney, Agent, or Firm* — Birch, Stewart, Kolasch & Birch, LLP

(57) ABSTRACT

The present disclosure aims to provide a method which, even when a protein complex is formed, can purify a protein derived from such a membrane protein complex by eluting the membrane protein complex maintaining its complex form. The present disclosure relates to a method for purifying a protein derived from a membrane protein complex, which includes: a protein binding step of binding to an antibody a membrane protein complex eluted from a membrane using a synthetic polymer; a protein eluting step of eluting the membrane protein complex bound to the antibody in the protein binding step at a pH of 6.0 or higher; and a synthetic polymer removing step of subjecting the membrane protein complex eluted in the protein eluting step to solvent extraction at a pH of 7.0 or lower to remove the synthetic polymer.

15 Claims, 4 Drawing Sheets

Surfactant

Synthetic polymer

Bilayer

Water

Monolayer

Water (a) Comparative
    Example 1          (b) Example 1          (c) Example 2
    ① ②                ① ②                  ① ②

①: Elution from           △: Eluted proteins
   Pre-antibody            ▲: Common to ① and ②
②: Elution from           ⧄: Antibody
   HRT-antibody            △: Protein observed only when
                              purified with HRT-antibody

① ②

①:Example 3(pH2.8)
②:Comparative Example 2(pH11)

pH Conditions (a)

Detection method: western blotting
①With non-specific antibody
②With specific antibody (b)  ①        ②

Detection method: silver staining
①With non-specific antibody
②With specific antibody

METHOD FOR PURIFYING PROTEIN DERIVED FROM MEMBRANE PROTEIN COMPLEX

TECHNICAL FIELD

The present disclosure relates to a method for purifying a protein derived from a membrane protein complex.

BACKGROUND ART

Surfactant-based methods have been actively used to elute membrane proteins from biological membranes.

SUMMARY OF DISCLOSURE

Technical Problem

As a result of extensive studies, however, the present inventors have found that conventional, widely used surfactant-based protein elution methods can decompose the structures of protein complexes formed on membranes, etc., resulting in separation and elution of individual proteins.

The present disclosure aims to solve the problem newly found by the present inventors and provide a method which, even when a protein complex is formed, can purify a protein derived from such a membrane protein complex by eluting the membrane protein complex while maintaining its complex form.

Solution to Problem

As a result of extensive studies on the above problem, the present inventors arrived at the idea of using synthetic polymers instead of surfactants. As shown in FIG. 1, the use of surfactants can decompose the structures of membrane protein complexes on biological membranes, resulting in separation and elution of individual proteins. This makes it difficult to reveal the relationship between the proteins. In contrast, when synthetic polymers, especially amphiphilic polymers, are used instead of surfactants, it has been found that membrane protein complexes can be eluted while maintaining their complex form, including membrane lipids. This is believed to be because synthetic polymers have a higher molecular weight than surfactants, and therefore it is possible to elute membrane protein complexes while maintaining their complex form without decomposing the structures of the complexes.

The present inventors then encountered a problem with the method for purifying a membrane protein complex that has been eluted using a synthetic polymer.

Since antibodies are often used to purify proteins, the present inventors studied antibody-based purification, i.e., a method of binding a specific protein alone to an antibody, separating this protein from the other proteins, and eluting the specific protein bound to the antibody. Moreover, although the use of an acidic solution is recommended to elute a protein bound to an antibody, no eluted protein was observed when an acidic solution was used for elution, if a synthetic polymer is used.

When facing this fact, the present inventors initially considered that the use of synthetic polymers prevents purification of proteins using antibodies. Surprisingly, however, they have discovered that the proteins can be eluted at a predetermined pH or higher (alkaline conditions) rather than under conventional acidic conditions. This is a remarkable discovery.

The present inventors have also found a new problem in that when elution of a protein from an antibody is performed under alkaline conditions, the elution itself is possible, but the alkaline conditions cause a significant reduction in the efficiency of removing the synthetic polymer in the subsequent step.

The present inventors have then found that, in a step of removing the synthetic polymer from the solution containing the eluted protein and synthetic polymer, the synthetic polymer can be efficiently removed under acidic conditions which destabilize the synthetic polymer.

In other words, the present disclosure has been completed based on these findings, etc., and relates to a method for purifying a protein derived from a membrane protein complex, the method including: a protein binding step of binding to an antibody a membrane protein complex eluted from a membrane using a synthetic polymer; a protein eluting step of eluting the membrane protein complex bound to the antibody in the protein binding step at a pH of 6.0 or higher; and a synthetic polymer removing step of subjecting the membrane protein complex eluted in the protein eluting step to solvent extraction at a pH of 7.0 or lower to remove the synthetic polymer.

Advantageous Effects of Disclosure

The method for purifying a protein derived from a membrane protein complex according to the present disclosure includes a protein binding step of binding to an antibody a membrane protein complex eluted from a membrane using a synthetic polymer; a protein eluting step of eluting the membrane protein complex bound to the antibody in the protein binding step at a pH of 6.0 or higher; and a synthetic polymer removing step of subjecting the membrane protein complex eluted in the protein eluting step to solvent extraction at a pH of 7.0 or lower to remove the synthetic polymer. Even when a protein complex is formed, this method can purify a protein derived from such a membrane protein complex by eluting the membrane protein complex maintaining its complex form. Eluting a membrane protein complex while maintaining its complex form enables elution of highly related proteins assembled as a complex as well as purification of individual proteins from the eluted membrane protein complex. Thus, if multiple proteins are purified, these proteins are found to form a complex on the membrane. Accordingly, the method of the present disclosure can provide information about, for example, which protein forms a complex with which protein on the membrane.

DESCRIPTION OF EMBODIMENTS

Figure 1:
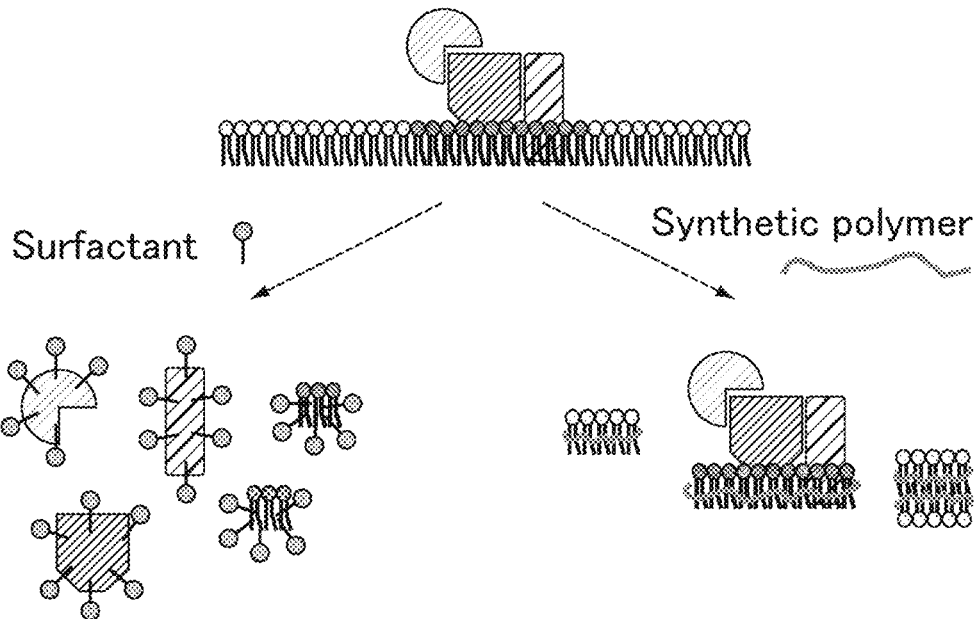
FIG. 1 is a schematic diagram showing exemplary processes for the elution of proteins, etc. using a surfactant or a synthetic polymer.

The method for purifying a protein derived from a membrane protein complex of the present disclosure includes a protein binding step of binding to an antibody a membrane protein complex eluted from a membrane using a synthetic polymer; a protein eluting step of eluting the membrane protein complex bound to the antibody in the protein binding step at a pH of 6.0 or higher; and a synthetic polymer removing step of subjecting the membrane protein complex eluted in the protein eluting step to solvent extraction at a pH of 7.0 or lower to remove the synthetic polymer.

Here, each of the steps may be performed multiple times, and another step may be performed between each of the steps.

(Protein Extracting Step)

First, a protein extracting step is described.

In the protein extracting step, a synthetic polymer is used to elute a membrane protein complex from a membrane. The use of a synthetic polymer enables elution of a membrane protein complex from a membrane while maintaining its complex form in which highly related proteins are assembled.

The term "complex form" herein refers to the form in which a group of proteins forming a homo- or hetero-dimer or multimer is bound to membrane-derived lipids.

The synthetic polymer used may be any polymer that is chemically synthesized. For example, amphiphilic polymers may be suitably used. Linear polymers are also preferred. These polymers may be used alone or in combinations of two or more.

Any amphiphilic polymer having both a hydrophilic portion and a hydrophobic portion in the polymer may be used. Examples include polymers in which hydrophobic monomers and hydrophilic monomers are polymerized randomly or blockwise, polymers in which monomers having both a hydrophilic group and a hydrophobic group are polymerized, polymers in which a hydrophilic side chain is bonded to a hydrophobic main chain, and polymers in which a hydrophobic side chain is bonded to a hydrophilic main chain. These may be used alone or in combinations of two or more. Preferred among these are polymers in which hydrophobic monomers and hydrophilic monomers are polymerized randomly or blockwise.

Examples of the polymers in which hydrophobic monomers and hydrophilic monomers are polymerized randomly or blockwise include:

polymers containing a unit derived from maleic acid, such as poly(styrene-maleic acid) (SMA, styrene-maleic acid polymer), poly(diisobutylene-maleic acid) (DIBMA, diisobutylene-maleic acid polymer), an isoprene-maleic acid polymer, and a butadiene-maleic acid polymer;

polymers containing a unit derived from fumaric acid, such as a styrene-fumaric acid polymer, a diisobutylene-fumaric acid polymer, an isoprene-fumaric acid polymer, and a butadiene-fumaric acid polymer;

polymers containing a unit derived from citraconic acid, such as a styrene-citraconic acid polymer, a diisobutylene-citraconic acid polymer, an isoprene-citraconic acid polymer, and a butadiene-citraconic acid polymer;

polymers containing a unit derived from mesaconic acid, such as a styrene-mesaconic acid polymer, a diisobutylene-mesaconic acid polymer, an isoprene-mesaconic acid polymer, and a butadiene-mesaconic acid polymer; and polymers containing a unit derived from aconitic acid, such as a styrene-aconitic acid polymer, a diisobutylene-aconitic acid polymer, an isoprene-aconitic acid polymer, and a butadiene-aconitic acid polymer. These may be used alone or in combinations of two or more. Preferred among these are polymers containing a unit derived from maleic acid, with poly(styrene-maleic acid) (SMA) or poly(diisobutylene-maleic acid) (DIBMA) being more preferred.

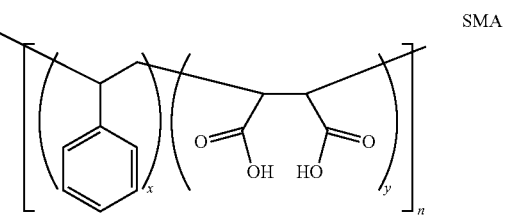

SMA

Poly(styrene-co-maleic acid)

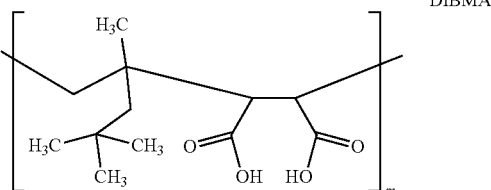

DIBMA

Poly(diisobutylene-alt-maleic acid)

The weight average molecular weight (Mw) of the synthetic polymer is preferably 3000 or higher, more preferably 5000 or higher, still more preferably 8000 or higher, particularly preferably 10000 or higher. The upper limit thereof is not limited but is preferably 100000 or lower, more preferably 50000 or lower, still more preferably 30000 or lower, particularly preferably 15000 or lower. When the weight average molecular weight is within the above range, the advantageous effect can be more suitably achieved. Particularly when the Mw is not lower than the lower limit, elution of a membrane protein complex can be more suitably enabled while maintaining its complex form in which highly related proteins are assembled.

The weight average molecular weight (Mw) herein can be determined with a gel permeation chromatograph (GPC) (GPC-8000 series available from Tosoh Corp., detector: differential refractometer, column: TSKGEL SUPERMULTIPORE HZ-M available from Tosoh Corp.) relative to polystyrene standards.

The membrane used may be any membrane in which a membrane protein complex is present, and may be a biological membrane, for example. Examples of the biological membrane include bilayers (lipid bilayers) such as cell membranes, outer mitochondrial membranes, inner mitochondrial membranes, nuclear membranes, endoplasmic reticulum membranes, Golgi apparatus membranes, lysosomal membranes, synaptic vesicle membranes, endosomal membranes, and peroxisomal membranes; and monolayers (lipid monolayers) such as rubber particles and lipid droplets. These may be used alone or in combinations of two or more. Preferred among these are monolayers, with rubber particles being more preferred. In other words, the membrane protein complex is preferably a membrane protein complex derived from a monolayer, more preferably a membrane protein complex derived from a rubber particle.

Figure 2:
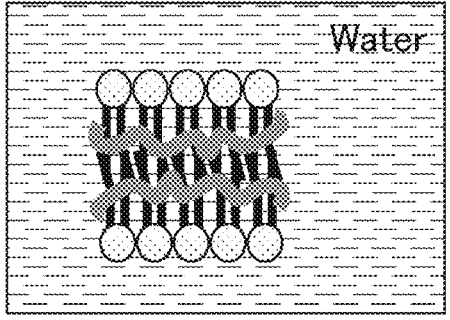
FIG. 2 is a schematic diagram showing exemplary processes for the elution of proteins, etc. using a synthetic polymer.
Figure 2:
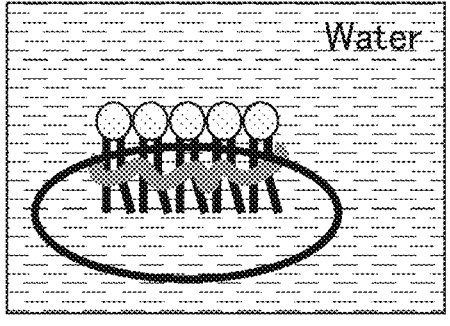

When proteins are eluted from a bilayer using a synthetic polymer, it is believed that no structural problem occurs because the hydrophobic portions of the lipids are present inside the membrane even if only a portion of the membrane is eluted, as shown in FIG. 2.

In contrast, it was considered that elution of proteins from a monolayer using a synthetic polymer might destabilize the membrane, unlike in the case of the bilayer, because the hydrophobic portions of the lipids could appear on the surface after the elution. In fact, however, no destabilization of concern was observed even when proteins were eluted from a monolayer using a synthetic polymer. This discovery that no destabilization occurs even when proteins are eluted from a monolayer using a synthetic polymer is a remarkable discovery beyond expectations of those skilled in the art.

The membrane protein complex refers to a complex formed by association of a plurality of membrane proteins attached to a membrane such as a biological membrane.

The expression "proteins attached to a membrane" herein means that, for example, the proteins, either fully or partially, are incorporated into the membrane or inserted into the membrane structure. However, this is not limited to these cases and also encompasses situations where, for example, they are localized on the surface of or inside the membrane. Furthermore, when they form a complex with a protein bound to the membrane and exist on the membrane as a complex, it is also included in the scope of the concept of being attached to the membrane.

Examples of membrane proteins that can form a membrane protein complex include proteins that are partially included in membranes, proteins that pass through membranes (transmembrane proteins), and proteins that are temporarily bound to these endogenous membrane proteins.

Specific examples of the membrane proteins include receptor, channel, transporter, pump, and enzyme proteins. The membrane proteins to be targeted may be membrane proteins that it is desired to elucidate their functions. For example, since the biosynthesis pathway of natural rubber is still unknown in many points, it is preferred to target proteins bound to rubber particles that are expected to biosynthesize natural rubber. In particular, prenyltransferase family proteins, which are presumed to play a central role in the biosynthesis of natural rubber but whose functions have not yet been fully elucidated, are preferred, with cis-prenyltransferase family proteins being more preferred, with cis-prenyltransferase family proteins derived from plants of the genus *Hevea* or *Taraxacum* being still more preferred. In other words, the membrane protein complex used preferably contains a prenyltransferase family protein, more preferably a cis-prenyltransferase family protein, still more preferably a cis-prenyltransferase family protein derived from a plant of the genus *Hevea* or *Taraxacum*.

Prenyltransferase family proteins include cis-prenyltransferase family proteins and trans-prenyltransferase family proteins. Preferred are cis-prenyltransferase family proteins.

The prenyltransferase family proteins or cis-prenyltransferase (CPT) family proteins may have any origin and may be derived from microorganisms, animals, or plants, preferably plants, more preferably plants of at least one selected from the group consisting of the genera *Hevea, Sonchus, Taraxacum*, and *Parthenium*, still more preferably plants of the genus *Hevea* or *Taraxacum*, particularly preferably *Hevea brasiliensis* or *Taraxacum kok-saghyz*, most preferably *Hevea brasiliensis*.

Examples of the plants include, but are not limited to, the genus *Hevea* such as *Hevea brasiliensis*; the genus *Sonchus* such as *Sonchus oleraceus, Sonchus asper*, and *Sonchus*

*brachyotus*; the genus *Solidago* such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea*, and *Solidago gigantea* Ait. var. *leiophylla* Fernald; the genus *Helianthus* such as *Helianthus annuus, Helianthus argophyllus, Helianthus atrorubens, Helianthus debilis, Helianthus decapetalus*, and *Helianthus giganteus*; the genus *Taraxacum* such as *Taraxacum, Taraxacum venustum* H. Koidz, *Taraxacum hondoense* Nakai, *Taraxacum platycarpum* Dahlst, *Taraxacum japonicum, Taraxacum officinale* Weber, *Taraxacum koksaghyz*, and *Taraxacum brevicorniculatum*; the genus *Ficus* such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L.f., *Ficus septica* Burm.f., and *Ficus benghalensis*; the genus *Parthenium* such as *Parthenium argentatum, Parthenium hysterophorus*, and *Ambrosia artemisiifolia* (*Parthenium hysterophorus*); lettuce (*Lactuca sativa*); *Ficus benghalensis; Arabidopsis thaliana*, etc.

The term "prenyltransferase (PT) family protein" herein refers to an enzyme that catalyzes the reaction of chain elongation of an isoprenoid compound.

Moreover, the term "trans-prenyltransferase (TPT) family protein" herein refers to an enzyme that catalyzes the reaction of trans-chain elongation of an isoprenoid compound.

Moreover, the term "cis-prenyltransferase (CPT) family protein" herein refers to an enzyme that catalyzes the reaction of cis-chain elongation of an isoprenoid compound.

CPT family proteins are characterized by having an amino acid sequence contained in the cis-IPPS domain (NCBI accession No. cd00475).

The term "isoprenoid compound" herein means a compound containing an isoprene unit ($C_5H_8$). Also, the term "cis-isoprenoid" refers to a compound including an isoprenoid compound in which isoprene units are cis-bonded, and examples include cis-farnesyl diphosphate, undecaprenyl diphosphate, and natural rubber.

Next, a method for eluting a membrane protein complex from a membrane using a synthetic polymer in the protein extracting step is described.

The method for eluting a membrane protein complex from a membrane using a synthetic polymer may be any method that can elute a membrane protein complex from a membrane using a synthetic polymer. For example, it may include bringing a synthetic polymer into contact with a membrane in a solution. Specifically, it may include mixing a synthetic polymer with a membrane in a solution.

The pH of the solution is preferably 6.0 or higher, more preferably 7.0 or higher, while it is preferably 10.0 or lower, more preferably 9.0 or lower, still more preferably 8.0 or lower. When it is within the above range, the advantageous effect tends to be more suitably achieved.

The pH herein is measured at 25° C.

The pH of the solution herein may be adjusted using a buffer. Here, any buffer may be used.

The temperature of the solution during mixing is preferably 1° C. or higher, more preferably 2° C. or higher, while it is preferably 15° C. or lower, more preferably 10° C. or lower, still more preferably 5° C. or lower. When it is within the above range, the advantageous effect tends to be more suitably achieved.

The mixing time is preferably 10 minutes or longer, more preferably 20 minutes or longer, still more preferably 30 minutes or longer. The upper limit thereof is not limited, but is preferably six hours or shorter, more preferably three hours or shorter, still more preferably one hour or shorter. When it is within the above range, the advantageous effect tends to be more suitably achieved.

The concentration of the synthetic polymer in the solution is preferably 0.5 g/L or higher, more preferably 3.0 g/L or higher, still more preferably 5.0 g/L or higher, particularly preferably 8.0 g/L or higher, most preferably 10.0 g/L or higher, while it is preferably 100 g/L or lower, more preferably 80.0 g/L or lower, still more preferably 50.0 g/L or lower, particularly preferably 30.0 g/L or lower, most preferably 15.0 g/L or lower. When it is within the above range, the advantageous effect tends to be more suitably achieved.

In the protein extracting step, the mixing of the synthetic polymer with the membrane in the solution is followed by separating the membrane from the protein solution. The membrane may be separated from the protein solution by centrifugation or filtration, for example. Then, the separated solution as a protein solution is subjected to the next step. (Protein Purification Carrier Preparing Step)

As described above, the specified method enables elution of highly related proteins assembled as a complex by eluting a membrane protein complex while maintaining its complex form. Further, as it enables purification of individual proteins from the eluted membrane protein complex, if multiple proteins are purified, these proteins are found to form a complex on the membrane. Accordingly, the specified method can provide information about, for example, which protein forms a complex with which protein on the membrane.

Thus, among the proteins contained in the protein solution obtained by the protein extracting step, the protein whose information is desired may be further purified.

Specifically, for example, in order to be able to purify the target protein, a protein purification carrier may be prepared according to a known method. The protein purification carrier may be prepared by any method and can be easily prepared by a person skilled in the art once the target protein is determined.

Specifically, an antibody capable of specifically binding to the target protein may be bound to a carrier such as beads. The antibody may be prepared, for example, by antigen processing of serum with the target protein.

Examples of the carrier include, but are not limited to, agarose resins (e.g., Affi-Gel®), methacrylate resins (e.g., TOYOPEARL®), and magnetic beads (e.g., Dynabeads®). These may be used alone or in combinations of two or more. (Protein Binding Step)

In the protein binding step, the membrane protein complex eluted from the membrane using the synthetic polymer is bound to an antibody. This enables separation of the target protein complex from the other membrane protein complexes eluted from the membrane using the synthetic polymer.

Specifically, as a protein purification carrier bound to an antibody that corresponds to the protein whose information is desired is prepared in the protein purification carrier preparing step to purify the protein whose information is desired from the other proteins contained in the protein solution obtained in the protein extracting step, this protein purification carrier can be used to separate the protein whose information is desired or the protein complex containing the protein whose information is desired from the other membrane protein complexes eluted from the membrane using the synthetic polymer.

In the protein binding step, for example, the protein solution obtained in the protein extracting step may be mixed with the protein purification carrier bound to the antibody. This allows the target protein capable of specifically binding to the antibody bound to the protein purification carrier, or the protein complex containing the target protein, to bind to the protein purification carrier, while the other proteins are not allowed to bind to the protein purification carrier. Thus, the target protein or the protein complex containing the target protein can be separated from the other proteins.

The pH of the solution is preferably 6.0 or higher, more preferably 6.5 or higher, still more preferably 7.0 or higher, while it is preferably 10.0 or lower, more preferably 9.0 or lower, still more preferably 8.0 or lower. When it is within the above range, the advantageous effect tends to be more suitably achieved.

The temperature of the solution during mixing is preferably 1° C. or higher, more preferably 2° C. or higher, while it is preferably 15° C. or lower, more preferably 10° C. or lower, still more preferably 5° C. or lower. When it is within the above range, the advantageous effect tends to be more suitably achieved.

The mixing time is preferably 10 minutes or longer, more preferably 20 minutes or longer, still more preferably 30 minutes or longer. The upper limit thereof is not limited, but is preferably three hours or shorter, more preferably two hours or shorter, still more preferably one hour or shorter. When it is within the above range, the advantageous effect tends to be more suitably achieved.

In the protein binding step, the mixing of the protein solution obtained in the protein extracting step with the protein purification carrier bound to the antibody is followed by collecting the solution as a flow-through fraction and subjecting the protein purification carrier separated from the solution to the next step.

Here, the protein purification carrier may be separated from the solution by centrifugation or filtration, for example.

Moreover, the protein purification carrier separated from the solution may optionally be washed, e.g., with a buffer, before the next step. (Protein Eluting Step)

In the protein eluting step, the membrane protein complex bound to the antibody in the protein binding step is eluted at a pH of 6.0 or higher. This enables separation of the antibody-bound membrane protein complex from the protein purification carrier. In particular, when the elution is carried out under alkaline conditions, the advantageous effect tends to be more suitably achieved. This is believed to be because elution under alkaline conditions allows the proteins to be eluted while stabilizing the synthetic polymer. In contrast, no proteins are eluted under acidic conditions. This is believed to be because elution under acidic conditions may insolubilize the synthetic polymer.

Specifically, for example, the protein purification carrier obtained in the protein binding step may be stirred in a solution having a pH of 6.0 or higher, preferably 8.0 or higher. This enables elution of the target protein bound to the protein purification carrier, or the protein complex containing the target protein, from the protein purification carrier.

The pH of the solution is preferably 7.0 or higher, more preferably 8.0 or higher, still more preferably 9.0 or higher, particularly preferably 10.0 or higher, most preferably 10.5 or higher. The upper limit thereof is not limited, but is preferably 12.0 or lower, more preferably 11.5 or lower. When it is within the above range, the advantageous effect tends to be more suitably achieved.

The temperature of the solution during mixing is preferably 1° C. or higher, more preferably 2° C. or higher, while it is preferably 15° C. or lower, more preferably 10° C. or lower, still more preferably 5° C. or lower. When it is within the above range, the advantageous effect tends to be more suitably achieved.

The mixing time is preferably 3 minutes or longer, more preferably 5 minutes or longer, still more preferably 10 minutes or longer. The upper limit thereof is not limited, but is preferably 1 hour or shorter, more preferably 40 minutes or shorter, still more preferably 20 minutes or shorter. When it is within the above range, the advantageous effect tends to be more suitably achieved.

The solution may contain a surfactant. The presence of a surfactant allows for elution of the antibody as well as the target protein or the protein complex containing the target protein. The use of a surfactant also allows for protein elution under neutral, not alkaline, conditions. Moreover, when a surfactant is used, heat treatment may optionally be performed. The heat treatment conditions may include, for example, 80 to 100° C. for 5 to 15 minutes.

Examples of the surfactant include anionic surfactants such as carboxylate surfactants, sulfonate surfactants, sulfate surfactants, and phosphate surfactants; nonionic surfactants such as polyoxyalkylene ether surfactants, polyoxyalkylene ester surfactants, polyhydric alcohol fatty acid ester surfactants, sugar fatty acid ester surfactants, alkyl polyglycoside surfactants, and polyoxyalkylene polyglucoside surfactants; and amphoteric surfactants such as amino acid surfactants, betaine surfactants, imidazoline surfactants, and amine oxide surfactants. These may be used alone or in combinations of two or more. Preferred among these are anionic surfactants.

In the protein eluting step, the stirring of the protein purification carrier obtained in the protein binding step in the solution having a pH of 6.0 or higher is followed by separating the protein purification carrier from the solution. The protein purification carrier may be separated from the solution by centrifugation or filtration, for example. Then, the separated solution as a protein elution fraction is subjected to the next step.

(Synthetic Polymer Removing Step)

In the synthetic polymer removing step, the membrane protein complex eluted in the protein eluting step is subjected to solvent extraction at a pH of 7.0 or lower to remove the synthetic polymer. This enables removal of the synthetic polymer and lipids from the membrane protein complex eluted in the protein eluting step and also improves the efficiency of protein extraction, facilitating protein detection. During this procedure, the membrane protein complex usually changes from its complex form to the presence of individual proteins. This is believed to be due to the removal of the synthetic polymer and lipids which contribute to maintaining the complex form.

Specifically, for example, the protein elution fraction solution obtained in the protein eluting step may be subjected to solvent extraction at a pH of 7.0 or lower to remove the proteins from the synthetic polymer and lipids.

The extraction may be performed by any method, preferably ether extraction or monohydric alcohol/halogenated hydrocarbon extraction, more preferably monohydric alcohol/halogenated hydrocarbon extraction, still more preferably methanol/chloroform extraction.

The pH of the solution is preferably 6.5 or lower, more preferably 6.0 or lower, still more preferably 5.0 or lower. The lower limit thereof is not limited, but is preferably 1.0 or higher, more preferably 2.0 or higher, still more preferably 2.8 or higher. When it is within the above range, the advantageous effect tends to be more suitably achieved.

The temperature of the solution during mixing is preferably 4° C. or higher, more preferably 10° C. or higher, still more preferably 15° C. or higher, while it is preferably 25° C. or lower, more preferably 20° C. or lower. When it is within the above range, the advantageous effect tends to be more suitably achieved.

The extraction time may be, but is not limited to, 5 to 10 minutes, for example.

In the synthetic polymer removing step, the solvent extraction is followed by collecting the proteins from which the synthetic polymer and lipids have been removed. Then, the obtained proteins are subjected to the next step.

(Protein Detecting Step)

In the protein detecting step, the proteins obtained in the synthetic polymer removing step are detected. This enables detection and identification of the proteins obtained in the synthetic polymer removing step.

The proteins may be detected by any method, such as electrophoresis (e.g., gel electrophoresis), immunochemical detection (e.g., Western blotting, ELISA, RIA), protein array (e.g., planar and bead-based systems), chromatographic separation, activity assay, and mass spectrometry. These may be used alone or in combinations of two or more. Preferred among these is electrophoresis, with SDS-PAGE being more preferred.

Qualitative analysis of the proteins in the protein detecting step provides information about, for example, which protein forms a complex with which protein on the membrane.

The method of the present disclosure enables the purification of not only artificially overexpressed proteins or proteins tagged for ease of purification but also natural proteins. In other words, the protein derived from a membrane protein complex of interest is preferably free from a tag for purification, more preferably a histidine tag.

EXAMPLES

The present disclosure is specifically described with reference to examples, but the present disclosure is not limited to the examples.

[Preparation of Rubber Particles]

Rubber particles were prepared from *Hevea* latex by 5-step centrifugation. To 900 mL of *Hevea* latex was added 100 mL of 1 M Tris-HCl buffer (pH 7.5) containing 20 mM dithiothreitol (DTT), whereby a latex solution was prepared. The latex solution was centrifuged stepwise at the following different centrifugal speeds: 1,000×g, 2,000×g, 8,000×g, 20,000×g, and 50,000×g. These centrifugation steps were each carried out at 4° C. for 45 minutes. The fractionated rubber particles were resuspended in a 1.5-fold amount of 100 M Tris-HCl buffer (pH 7.5) containing 2 mM dithiothreitol (DTT).

[Protein Extracting Step] (Elution of Membrane Protein Complex from Rubber Particles)

To 50 mg of poly(diisobutylene-maleic acid) (DIBMA) (Mw=12,000, available from Cube Biotech) was added 500 μL of ultrapure water, whereby a 10% DIBMA solution was prepared. Then, 100 μL of a 20% rubber particle solution, 50 μL of the 10% DIBMA solution, and 250 μL of 100 mM Tris-HCl buffer (pH 7.5) were mixed (total: 400 μL, final DIBMA concentration: 12.5 g/L), and inversion mixing was continued at 4° C. for one hour.

To separate the rubber particles from the protein solution, the elution procedure was followed by ultracentrifugation at 1,000,000×g for 45 minutes at 4° C. The separated aqueous layer was used as a protein solution.

US 12,606,807 B2

11

[Protein Purification Carrier (Protein Purification Beads) Preparing Step]

The beads used for protein purification were prepared by coupling an antibody to Dynabeads M-270 Epoxy according to the manual of the Dynabeads Co-Immunoprecipitation Kit (available from VERITAS Corporation). As the antibody to be coupled, two types of antibodies were provided: an antibody purified from rabbit serum before antigen processing (pre-antibody); and an antibody purified from rabbit serum that had undergone antigen processing with a HRT1 peptide (cis-prenyltransferase family protein derived from *Hevea brasiliensis*) (HRT1-antibody). Each antibody was bound to the beads (pre-antibody-bound beads, HRT1-antibody-bound beads).

[Protein Binding Step (Protein Purification (Co-Immunoprecipitation))]

To 1.5 mg of the antibody-bound beads prepared above were added 200 µL of the protein solution obtained by eluting the proteins from the rubber particles and 200 µL of 100 mM Tris-HCl (pH 7.5), and inversion mixing was performed at 4° C. for one hour to bind the proteins to the antibody.

After the one-hour inversion mixing, the aqueous layer was collected as a flow-through fraction. The remaining antibody-bound beads were washed three times with 400 µL of 100 mM Tris-HCl (pH 7.5) and then washed by inversion mixing with 400 µL of 100 mM Tris-HCl (pH 7.5) containing 0.02% Tween 20 for 10 minutes.

[Protein Eluting Step]

Comparative Example 1

To the washed beads was added 60 µL of 50 mM glycine buffer (pH 2.8), followed by inversion mixing at 4° C. for 10 minutes. After the mixing, the aqueous layer was used as a protein elution fraction.

Example 1

To the washed beads was added 60 µL of 500 mM NH₄OH (pH 11.0), followed by inversion mixing at 4° C. for 10 minutes. After the mixing, the aqueous layer was used as a protein elution fraction.

Example 2

To the washed beads was added 60 µL of 1×SDS sample buffer (62.5 mM Tris-HCl (pH 6.8), 50 mM dithiothreitol (DTT), 2% sodium dodecyl sulphate (SDS), 5% sucrose, 0.005% bromophenol blue (BPB)), followed by heat treatment at 98° C. for 10 minutes. After the heat treatment, the aqueous layer was used as a protein elution fraction.

[Synthetic Polymer Removing Step]

Comparative Example 1

To remove the synthetic polymer and lipids, 60 µL of the eluted protein solution was subjected to methanol/chloroform extraction. To 60 µL of the protein solution was added 240 µL (four times the volume of the sample) of a cold methanol solution, and they were mixed using a vortex mixer. Further, 60 µL (the same volume as the sample) of a cold chloroform solution was added, and they were mixed using the vortex mixer. Finally, 180 µL (three times the volume of the sample) of a cold ultrapure water was added, and they were mixed using the vortex mixer. The mixture was centrifuged at 15,000×g for three minutes so that it was separated into two layers, and then the aqueous layer (upper layer) was removed. The remaining organic (lower) layer and protein layer were again combined and mixed with 240 µL (4 times the volume of the sample) of a cold methanol solution. The solution was centrifuged once at 5,000×g for one minute and then directly centrifuged at 20,000×g for five minutes. After the centrifugation, the organic layer was removed and the remaining protein pellets were completely dried. The dried protein pellets were redissolved in 30 µL of 1×SDS sample buffer. All of these treatments were carried out at 18° C. After the redissolution, heat treatment was performed at 98° C. for 10 minutes.

Examples 1 and 2

The eluted protein solution was combined with 1 M acetic acid buffer (pH 3.5) to acidify the solution, followed by methanol/chloroform extraction. Here, the methanol/chloroform extraction was carried out as in Comparative Example 1 except for the pH.

[Protein Detecting Step (Silver Staining)]

Protein detection was determined by SDS-PAGE. The separation gel used was a 15% acrylamide gel. Protein staining was performed by silver staining using Si1-Best Stain One (available from NACALAI TESQUE, INC.). The results are shown in FIG. 3.

Figure 3:
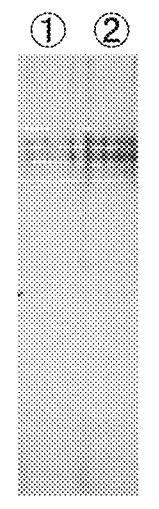
FIG. 3 is a diagram showing the results of Comparative Example 1 and Examples 1 and 2.
Figure 3:
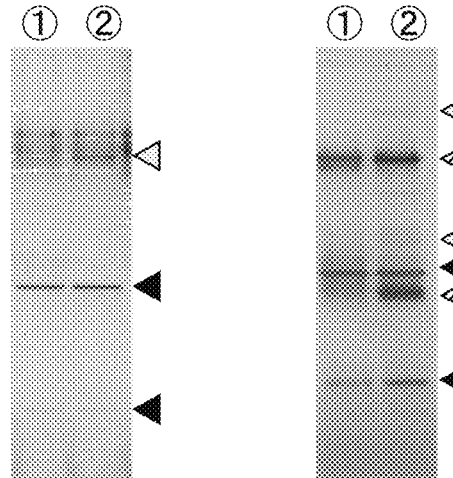

In Comparative Example 1, no protein elution was observed in the elution fraction when the immunoprecipitation was carried out using either the pre-antibody or the HRT-antibody (FIG. 3(*a*)). In contrast, in Example 1, protein elution was observed when the immunoprecipitation was carried out using either the pre-antibody or the HRT-antibody (FIG. 3(*b*)). Moreover, as there were differences in the eluted proteins between using the pre-antibody and the HRT-antibody, it is considered that co-immunoprecipitation using the HRT-antibody was achieved. Moreover, in Example 2, protein elution was also observed when the immunoprecipitation was carried out using either the pre-antibody or the HRT-antibody (FIG. 3(*c*)). However, in these cases, the antibodies used for purification were also eluted together.

Examples 1 and 2 showed differences in the pattern of eluted proteins between using the pre-antibody and the HRT-antibody. This demonstrates that purification of arbitrary proteins was achieved using the antibody.

In addition, two or more protein bands, not a single band, were observed as the eluted proteins. If the proteins are eluted individually with the synthetic polymer, only a single band (only HRT) should be detected. Thus, the elution of multiple bands demonstrates that elution of the proteins in complex form was achieved.

These results demonstrate success in solubilizing proteins in complex form from rubber particles (monolayer) using a synthetic polymer and purifying a complex containing arbitrary proteins using an antibody.

Comparative Example 1 was further examined to confirm that no proteins were eluted from the beads at a pH of 2.8.

[Effect of pH in Synthetic Polymer Removing Step (Experiment to Compare Efficiency of Methanol/Chloroform Extraction at Each pH)]

Comparative Example 2 (Alkaline Conditions)

To 50 µL of the protein solution eluted from rubber particles described above was added 150 µL of 500 mM NH₄OH (pH 11.0), and they were mixed using a vortex mixer to adjust the pH of the solution to 11.0.

Figure 4:
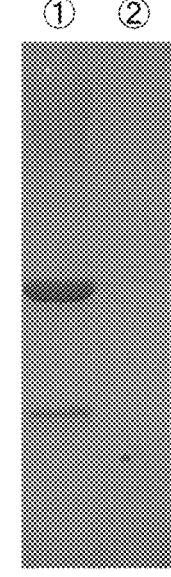
FIG. 4 is a diagram showing the results of Comparative Example 2 and Example 3.

The solution was left to stand for five minutes, followed by methanol/chloroform extraction performed as in Comparative Example 1 except for the pH, thereby removing the synthetic polymer and lipids. Then, the protein amount was determined by SDS-PAGE. The gel was stained with Coomassie Brilliant Blue (CBB). The results are shown in FIG. 4.

Example 3 (Acidic Conditions)

To 50 μL of the protein solution eluted from rubber particles described above was added 150 μL of 50 mM glycine-HCl buffer (pH 2.8), and they were mixed using a vortex mixer to adjust the pH of the solution to 2.8.

The solution was left to stand for five minutes, followed by methanol/chloroform extraction performed as in Comparative Example 1 except for the pH, thereby removing the synthetic polymer and lipids. The, the protein amount was determined by SDS-PAGE. The gel was stained with Coomassie Brilliant Blue (CBB). The results are shown in FIG. 4.

FIG. 4 shows that even though the same procedure was performed on the same protein solution, proteins were detected under acidic conditions (Example 3), while almost no proteins were detected under alkaline conditions. This indicates that acidifying the solution is better.

[Effect of pH in Synthetic Polymer Removing Step (Experiment to Compare Efficiency of Methanol/Chloroform Extraction at Each pH (the Same Buffer Composition Except for the pH))]

In the previous comparative experiment, as different regents were used to adjust the pH, the composition of the reagent used may affect the results. Thus, experiments were performed using buffers of the same composition.

Comparative Example 3 (Alkaline Conditions)

To 25 μL of the protein solution eluted from rubber particles described above was added 75 μL of 200 mM Trisi-acetic acid buffer (pH 9.0), and they were mixed using a vortex mixer to adjust the pH of the solution to 9.0.

Figure 5:
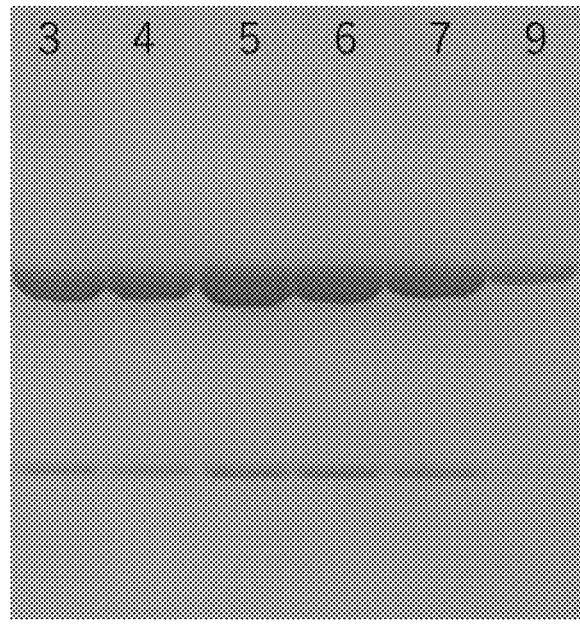
FIG. 5 is a diagram showing the experimental results depending on the pH conditions.

The solution was left to stand for five minutes, followed by methanol/chloroform extraction performed as in Comparative Example 1 except for the pH, thereby removing the synthetic polymer and lipids. Then, the protein amount was determined by SDS-PAGE. The gel was stained with Coomassie Brilliant Blue (CBB). The results are shown in FIG. 5.

Example 4 (Neutral Conditions)

To 25 μL of the protein solution eluted from rubber particles described above was added 75 μL of 200 mM Trisi-acetic acid buffer (pH 7.0), and they were mixed using a vortex mixer to adjust the pH of the solution to 7.0.

The solution was left to stand for five minutes, followed by methanol/chloroform extraction performed as in Comparative Example 1 except for the pH, thereby removing the synthetic polymer and lipids. Then, the protein amount was determined by SDS-PAGE. The gel was stained with Coomassie Brilliant Blue (CBB). The results are shown in FIG. 5.

Example 5 (Acidic Conditions)

To 25 μL of the protein solution eluted from rubber particles described above was added 75 μL of 200 mM Trisi-acetic acid buffer (pH 3.0, 4.0, 5.0, or 6.0), and they were mixed using a vortex mixer to adjust the pH of the solution to 3.0, 4.0, 5.0, or 6.0.

The solution was left to stand for five minutes, followed by methanol/chloroform extraction performed as in Comparative Example 1 except for the pH, thereby removing the synthetic polymer and lipids. Then, the protein amount was determined by SDS-PAGE. The gel was stained with Coomassie Brilliant Blue (CBB). The results are shown in FIG. 5.

FIG. 5 shows that when methanol/chloroform extraction was performed under acidic to neutral conditions (pH 3.0 to 7.0), little change in protein amount was found. In contrast, when the extraction was performed under alkaline conditions (pH 9.0), a decrease in protein amount was observed. This is considered to be because the acidic conditions destabilized the synthetic polymer and thereby promoted decomposition of the synthetic polymer and the complex of lipids and proteins, resulting in an increase in the efficiency of methanol/chloroform extraction.

Figure 6:
FIG. 6 is a diagram showing the experimental results with the differences between using a nonspecific antibody and a specific antibody.
Figure 6:
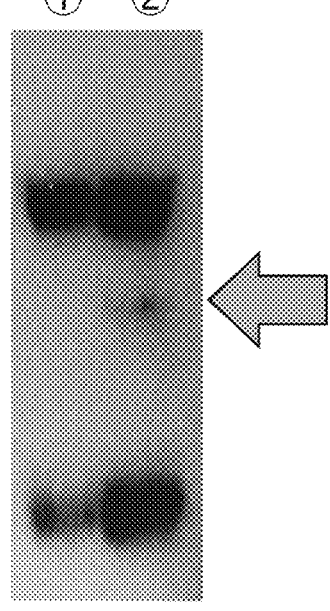
Figure 6:
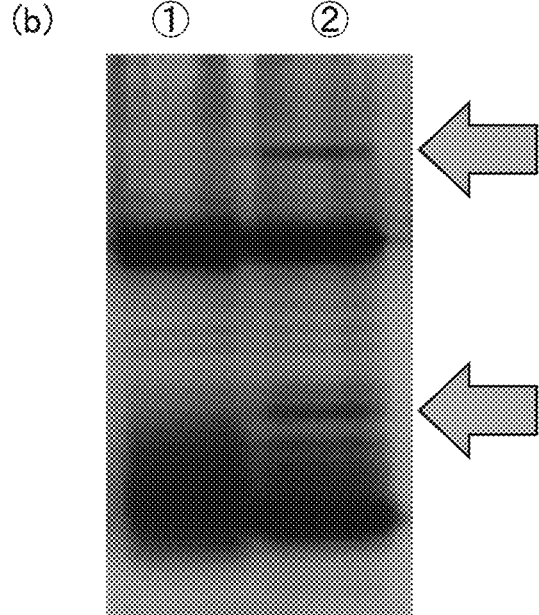

To confirm whether the target proteins were specifically purified, each elution fraction was subjected to western blotting using the HRT-antibody. The results are shown in FIG. 6.

The protein solution eluted via the pre-antibody and the protein solution eluted via the HRT-antibody were each subjected to SDS-PAGE using a 15% acrylamide gel, and then the proteins were transferred to a PVDF membrane using Trans-Blot Turbo Transfer System (Bio Rad) at 25 V and 1.0 A for 30 minutes. After the transfer, the PVDF membrane was washed with PBS- and then blocked overnight at 4° C. using PVDF Blocking Reagent for Can Get Signal (TOYOBO).

After the blocking, the PVDF membrane was washed with PBS-T and then impregnated with a mixture of 5 mL of Solution 1 for primary antibody of Can Get Signal Immunoreaction Enhancer Solution (TOYOBO) with 2.5 μL of a 1 mg/mL HRT-antibody solution (2000-fold dilution) for 10 minutes at room temperature to perform a primary antibody reaction. After the primary antibody reaction, the PVDF membrane was again washed with PBS-T to wash away excess antibody.

After the washing, the PVDF membrane was impregnated with a mixture of 5 mL of Solution 2 for secondary antibody of Can Get Signal Immunoreaction Enhancer Solution with 0.5 μL of H Anti-IgG (H+L Chain) (Rabbit) pAb-HRP Goat IgG antibody (10000-fold dilution) for 10 minutes at room temperature to perform a secondary antibody reaction. After the secondary antibody reaction, the PVDF membrane was again washed with PBS-T to wash away excess antibody.

Antibody detection was performed using Amersham ECL Prime Western Blotting Detection Reagent by detecting the luminescence produced by horseradish peroxidase (HRP) conjugated to the secondary antibody using a photosensitive film.

As shown in FIG. 6, specific bands were detected only in the protein solution eluted via the HRT-antibody. This demonstrates that the use of a specific antibody enables the purification of arbitrary proteins according to the purpose.

Exemplary embodiments of the present disclosure include:

Embodiment 1. A method for purifying a protein derived from a membrane protein complex, the method comprising:

a protein binding step of binding to an antibody a membrane protein complex eluted from a membrane using a synthetic polymer;

a protein eluting step of eluting the membrane protein complex bound to the antibody in the protein binding step at a pH of 6.0 or higher; and a synthetic polymer removing step of subjecting the membrane protein complex eluted in the protein eluting step to solvent extraction at a pH of 7.0 or lower to remove the synthetic polymer.

Embodiment 2. The method for purifying a protein derived from a membrane protein complex according to Embodiment 1, wherein the synthetic polymer is an amphiphilic polymer.

Embodiment 3. The method for purifying a protein derived from a membrane protein complex according to Embodiment 1, wherein the synthetic polymer is a polymer containing a unit derived from maleic acid.

Embodiment 4. The method for purifying a protein derived from a membrane protein complex according to Embodiment 1, wherein the synthetic polymer is poly(styrene-maleic acid) (SMA) or poly(diisobutylene-maleic acid) (DIBMA).

Embodiment 5. The method for purifying a protein derived from a membrane protein complex according to any combination with any one of Embodiments 1 to 4, wherein in the protein eluting step, the membrane protein complex is eluted at a pH of 9.0 or higher.

Embodiment 6. The method for purifying a protein derived from a membrane protein complex according to any combination with any one of Embodiments 1 to 4, wherein in the protein eluting step, the membrane protein complex is eluted using a surfactant.

Embodiment 7. The method for purifying a protein derived from a membrane protein complex according to any combination with any one of Embodiments 1 to 6, wherein the membrane protein complex is a membrane protein complex derived from a monolayer.

Embodiment 8. The method for purifying a protein derived from a membrane protein complex according to Embodiment 7, wherein the monolayer is a rubber particle.

Embodiment 9. The method for purifying a protein derived from a membrane protein complex according to any combination with any one of Embodiments 1 to 8, wherein the membrane protein complex contains a pre-nyltransferase family protein.

Embodiment 10. The method for purifying a protein derived from a membrane protein complex according to any combination with any one of Embodiments 1 to 9, wherein the membrane protein complex contains a cis-prenyltransferase family protein.

Embodiment 11. The method for purifying a protein derived from a membrane protein complex according to any combination with any one of Embodiments 1 to 10, wherein the membrane protein complex contains a cis-prenyltransferase family protein derived from a plant of the genus *Hevea* or *Taraxacum*.

The invention claimed is:

1. A method for purifying a protein obtained from a membrane protein complex of *Hevea* latex, the method comprising:

a protein binding step of binding to an antibody a membrane protein complex eluted from a membrane using a amphiphilic polymer;

a protein eluting step of eluting the membrane protein complex bound to the antibody in the protein binding step at a pH of 6.0 or higher; and a amphiphilic polymer removing step of subjecting the membrane protein complex eluted in the protein eluting step to solvent extraction at a pH of 7.0 or lower to remove the amphiphilic polymer.

2. The method for purifying a protein obtained from a membrane protein complex according to claim 1, wherein the amphiphilic polymer is a polymer containing a unit obtained from maleic acid.

3. The method for purifying a protein obtained from a membrane protein complex according to claim 1, wherein the amphiphilic polymer is poly(styrene-maleic acid) (SMA) or poly(diisobutylene-maleic acid) (DIBMA).

4. The method for purifying a protein obtained from a membrane protein complex according to claim 1, wherein in the protein eluting step, the membrane protein complex is eluted at a pH of 9.0 or higher.

5. The method for purifying a protein obtained from a membrane protein complex according to claim 1, wherein in the protein eluting step, the membrane protein complex is eluted using a surfactant.

6. The method for purifying a protein obtained from a membrane protein complex according to claim 1, wherein the membrane protein complex is a membrane protein complex obtained from a monolayer.

7. The method for purifying a protein obtained from a membrane protein complex according to claim 6, wherein the monolayer is a rubber particle.

8. The method for purifying a protein obtained from a membrane protein complex according to claim 1, wherein the membrane protein complex contains a pre-nyltransferase family protein.

9. The method for purifying a protein obtained from a membrane protein complex according to claim 1, wherein the membrane protein complex contains a cis-prenyltransferase family protein.

10. The method for purifying a protein obtained from a membrane protein complex according to claim 1, wherein the membrane protein complex contains a cis-prenyltransferase family protein obtained from a plant of the genus *Hevea* or *Taraxacum*.

11. The method for purifying a protein obtained from a membrane protein complex according to claim 1, wherein the membrane protein complex contains a cis-prenyltransferase (CPT) family protein obtained from *Hevea brasiliensis* or *Taraxacum kok-saghyz*.

12. The method for purifying a protein obtained from a membrane protein complex according to claim 1, wherein the membrane protein complex contains HRT1, obtained from *Hevea brasiliensis*.

13. The method for purifying a protein obtained from a membrane protein complex according to claim 9, wherein the cis-prenyltransferase enzyme comprises an amino acid sequence contained in a cis-IPPS domain (NCBI accession No. cd00475).

14. The method for purifying a protein obtained from a membrane protein complex according to claim 11, wherein the cis-prenyltransferase enzyme comprises an amino acid sequence contained in a cis-IPPS domain (NCBI accession No. cd00475).

15. The method for purifying a protein obtained from a membrane protein complex according to claim 11, wherein the protein purified is HRT1 obtained from rubber particles.

* * * * *